United States Patent
Wang et al.

[11] Patent Number: 5,830,441
[45] Date of Patent: Nov. 3, 1998

[54] PHOTOSTABLE UV ABSORBENT CONTAINING A-CYANO CINNAMYL MOIETY

[75] Inventors: Chenjie Wang, Livingston; Ratan K. Chaudhuri, Lincoln Park, both of N.J.; Janusz Jachowicz, Bethel, Conn.; Bruce C. Locke, Easton, Pa.; Frank M. Miksza, Colonia, N.J.

[73] Assignee: ISP Investments Inc., Wilmington, Del.

[21] Appl. No.: 9,173

[22] Filed: Jan. 20, 1998

[51] Int. Cl.$^6$ .............................. A61K 7/42; G07C 255/03
[52] U.S. Cl. .............................. 424/59; 424/60; 424/400; 424/401; 558/401; 558/402
[58] Field of Search ................. 424/59, 60, 400, 424/407; 558/401, 402

[56] References Cited

U.S. PATENT DOCUMENTS

| | | | |
|---|---|---|---|
| 4,284,621 | 8/1981 | Preuss | 424/60 |
| 4,699,779 | 10/1987 | Palinczar | 424/59 |
| 5,338,539 | 8/1994 | Raspanti | 424/59 |
| 5,567,418 | 10/1996 | Forestier et al. | 558/407 |

*Primary Examiner*—Johann Richter
*Assistant Examiner*—Ebenezer Sackey
*Attorney, Agent, or Firm*—Marilyn J. Maue; William J. Davis; Walter Katz

[57] ABSTRACT

A photostable UV absorbent with maximum absorption above 340 nm having the formula:

wherein

R is —$CO(R_2)$ or phenyl optionally substituted with lower alkyl and/or lower alkoxy;

$R_2$ is —alkyl, —$O(C_{2+}$ alkyl), $$-N(R_3)-(CH_2)_n-N\begin{matrix}R_4\\R_5\end{matrix} \quad \text{or}$$

$$-N(R_3)-(CH_2)_n-N^+-R_5 \quad . \quad A^-;$$
with $R_4$ and $R_6$ n has a value of from 2 to 8;

S and T each independently are hydroxy, lower alkyl, lower alkoxy or, when $R_2$ is alkyl or alkoxy, S can also be phenyl and when $R_2$ is alkoxy, T is alkoxy, or S+T taken with the phenyl ring form a naphthyl radical or a fused benzodioxol-5-yl heterocyclic radical;

k+l has a value of from 0 to 3 with the proviso that, when $R_2$ is —O(alkyl), T is —O(lower alkyl) and the value of l is 2 or 3;

$R_3$ is hydrogen or lower alkylene;

$R_4$, $R_5$, and $R_6$ are each independently $C_1$ to $C_{18}$ alkyl or one of $R_4$, $R_5$ and $R_6$ can be phenyl and A is an anion.

23 Claims, 3 Drawing Sheets

PHOTOSTABLE UV ABSORBENT CONTAINING A-CYANO CINNAMYL MOIETY

FIELD OF THE INVENTION

The present invention relates to active UV absorption agents having a maximum absorption above 340 nm wavelength and having improved stability and solubility in polar organic solvents and other formulating components. Instant absorption agents are highly effective in protecting the skin or hair against damage caused by the most harmful UV radiation.

BACKGROUND OF THE INVENTION

Solar radiation is generally classified as UV-C in the range of 200–280 nm which is effectively filtered by the ozone layer; UV-B in the range of 290–320 nm which causes skin tanning and UV-A in the range of 320–400 nm. UV-A is subdivided into regions UV-A I at 320 to 340 nm and UV-A II at 340 to 400 nm wavelength. While people with highly sensitive skin may suffer sunburn at radiation as low as 335–340 nm, those of normal skin sensitivity or darker skinned individuals can tolerate higher radiation; however, even these individuals are subject to skin damage caused by solar radiation above 340 nm. In addition to causing sunburn and brown age spots, radiation above 340 nm is associated with premature skin aging such as loss of skin elasticity and wrinkle formation. Also, radiation at these high levels has been particularly identified as a leading cause of skin cancer. A few methoxyphenol ketones which initially possess maximum absorption at about 350 nm, notably avobenzone (PARSOL® 1789) have been proposed as sunscreening agents, however, these have been found to lack stability and photodegrade upon exposure to illumination within a short time, e.g. less than 0.5 hour, to 250 nm maximum absorption and little or no absorption above 300 nm. Accordingly it is desirable to develop a sunscreen which is stable and selectively effective against radiation above 340 nm, particularly with a maximum absorption in the range of 345–365 nm, which is photostable but non-toxic and which is economical to produce. As a sunscreen, the desired chemical should be odorless and substantially colorless over an extended period of use. The present invention achieves these objectives with a group of chemicals economically produced in a one-step process.

An object of this invention is to provide a compound specifically directed to radiation absorption in the 345–365 nm wavelength range.

Another object is to provide a sunscreen which has extended solubility in polar solvents and which exhibits a capability of hydrogen bonding with other components of a personal care formulation.

Still another object is to provide a sunscreen having improved hair and skin substantivity.

These and other benefits and advantages of the present invention will become apparent from the following description and disclosure.

THE INVENTION

For the purpose of this invention "lower alkyl", "lower alkoxy" and "lower alkylene" are radicals containing 1 to 4 carbon atoms. Where "alkyl" is not otherwise characterized, the radical includes 1 to 18 carbon atoms.

In accordance with this invention there is provided a photostable sunscreening agent effective in the range above 340 nm wavelength having the formula:

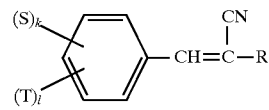

wherein
R is —CO($R_2$) or phenyl optionally substituted with lower alkyl and/or lower alkoxy;
$R_2$ is —alkyl, —)($C_{2+}$ alkyl),

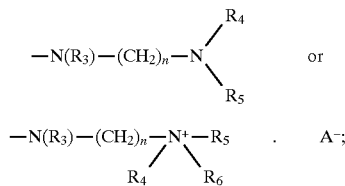

n has a value of from 2 to 8;
S and T each independently are hydroxy, lower alkyl, lower alkoxy or, when $R_2$ is alkyl or alkoxy, S can also be phenyl and when $R_2$ is alkoxy, T is alkoxy or S+T taken with the phenyl ring forms a naphthyl radical or a fused benzodioxol-5-yl heterocyclic radical;
k+l has a value of from 0 to 3 with the proviso that, when $R_2$ is —O(alkyl), T is —O(lower alkyl) and the value of l is at least 2;
$R_3$ is hydrogen or lower alkylene;
$R_4$, $R_5$ and $R_6$ are each independently $C_1$ to $C_{18}$ alkyl or one of $R_4$, $R_5$ and $R_6$ can be phenyl and
A is an anion.

Representative compounds of the above formula include cyanocinnamate esters, such as the polyalkoxy substituted species

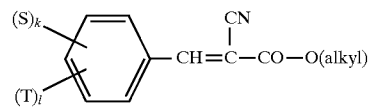

| | $\lambda_{max}$ (nm) | $\epsilon$ | $E_1$ |
|---|---|---|---|
| Methyl α-cyano-3,4-dimethoxy cinnamate | 359 | 23,000 | 930 |
| Ethyl α-cyano-3,4-dimethoxy cinnamate | 359 | 24,000 | 920 |
| Ethyl α-cyano-2,4-dimethoxy cinnamate | 363 | 36,000 | 1380 |
| Ethyl α-cyano-3,4,5-trimethoxy cinnamate | 345 | 20,000 | 690 |
| Ethyl α-cyano-3,4-methylenedioxy cinnamate | 361 | 22,300 | 910 |
| Ethyl α-cyano-3-methoxy-4-hydroxy cinnamate | 364 | 25,700 | 1040 |
| Propyl α-cyano-3,4-dimethoxy cinnamate | 359 | 23,650 | 860 |
| Isopropyl α-cyano-3,4-dimethoxy cinnamate | 359 | 23,650 | 860 |
| Ethyl α-cyano-3-methyl-5-methoxy cinnamate | 348 | | |
| Butyl α-cyano-3,4-dimethoxy cinnamate | 359 | 23,100 | 800 |
| Pentyl α-cyano-3,4-dimethoxy cinnamate | 359 | 23,600 | 780 |
| Isoamyl α-cyano-3,4-dimethoxy cinnamate | 359 | 23,600 | 780 |
| Isoamyl α-cyano-3,5-dimethoxy cinnamate | 365 | 25,100 | 870 |
| Isoamyl α-cyano-3,4-ethoxy cinnamate | 361 | 19,250 | 670 |
| Isoamyl α-cyano-3,-methylenedioxy cinnamate | 361 | 19,250 | 670 |
| Hexyl α-cyano-3,4-dimethoxy cinnamate | 359 | 24,100 | 760 |
| Heptyl α-cyano-3,4-dimethoxy cinnamate | 359 | 23,800 | 720 |
| Octyl α-cyano-3,4-dimethoxy cinnamate | 359 | 23,400 | 680 |
| 2-Ethylhexyl α-cyano-3,4-dimethoxy cinnamate | 359 | 23,400 | 680 |
| Decyl α-cyano-3,4-dimethoxy cinnamate | 359 | 23,100 | 620 |
| Dodecyl α-cyano-3,4-dimethoxy cinnamate | 359 | 23,600 | 590 |
| Hexadecyl α-cyano-3,4-dimethoxy cinnamate | 359 | 21,300 | 470 |

Of the above species, the branched alkyl esters of at least 4 carbon atoms in the alkyl group are preferred. the α-phenyl cinnamonitrile species

| | λmax (nm) | ε | E₁ |
|---|---|---|---|
| (S)ₖ—[phenyl]—CH=C(CN)—[phenyl]—(S)ₖ with (T)ₗ substituents | | | |
| α-Phenyl-3,4-dimethoxy cinnamonitrile | 347 | 22,500 | 850 |
| α-Tolyl-3,4-dimethoxy cinnamonitrile | 348 | 22,100 | 910 |
| α-4'-methoxyphenyl-3,4-dimethoxy cinnamonitrile | 353 | 29,000 | 980 |
| α-3',4'-dimethoxyphenyl-3,4-dimethoxy cinnamonitrile | 359 | 26,000 | 800 |
| α-4'-methoxyphenyl-4-methoxy cinnamonitrile | 343 | 29,500 | 1110 |
| α-3',4'-dimethoxyphenyl-4-methoxy cinnamonitrile | 350 | 27,500 | 930 |
| α-3',4'-dimethoxyphenyl-3-ethoxy cinnamonitrile | 350 | 27,500 | 930 |
| α-3',4'-dimethoxyphenyl-4-isopropyl cinnamonitrile | 343 | 22,400 | 730 |
| α-3',4'-dimethoxyphenyl-4-phenyl cinnamonitrile | 355 | 29,600 | 870 |
| α-4'-methoxyphenyl-2,4-dimethoxy cinnamonitrile | 356 | 25,300 | 860 |
| the ketone species | | | |
| (S)ₖ—[phenyl]—CH=C(CN)—CO(alkyl) with (T)ₗ | | | |
| t-Butyl α-cyano 3,4-dimethoxy cinnamyl ketone | 367 | 19,100 | 700 |
| t-Butyl α-cyano 4-methoxy cinnamyl ketone | 348 | 24,000 | 990 |
| t-Butyl α-cyano 4-phenyl cinnamyl ketone | 343 | 29,500 | 1020 |
| iso-propyl α-cyano-phenyl cinnamyl ketone | — | — | — |
| n-butyl α-cyano 4-phenyl cinnamyl ketone | — | — | — |
| the α-cyano cinnamide species | | | |
| (S)ₖ—[phenyl]—CH=C(CN)—N(R₃)—(CH₂)ₙ—N(R₄)(R₅) with (T)ₗ | | | |
| Dimethylamino N-propyl α-cyano-3,4-dimethoxy cinnamide | 353 | 23,400 | 740 |
| Dimethylamino N-propyl α-cyano-4-methoxy cinnamide | — | — | — |
| the quaternized α-cyano cinnamide species | | | |
| (S)ₖ—[phenyl]—CH=C(CN)—N(R₃)—(CH₂)ₙ—N⁺(R₄)(R₅)(R₆)·A with (T)ₗ | | | | including dodecyl tosylate quaternized N,N,N-dimethyl propyl amino propyl α-cyano-3,4-dimethoxy cinnamide, dodecyl tosylate quaternized N,N,N-dimethyl propyl amino propyl α-cyano 4-methoxy cinnamide, chloride or bromide quaternized N,N,N-dimethyl ethyl amino butyl α-cyano 3-methoxy cinnamide, trimethyl ammonium chloride quaternized N,N,N-diethyl methyl amino hexyl α-cyano α-cyano 3,4,5-trimethoxy cinnamide, lauryl sulfonate quaternized N,N,N-dimethyl dodecyl amino propyl α-cyano 3,5-diethoxy cinnamide, tosylate quaternized dimethyl octyl amino propyl β-methyl-α-cyano 3,4-dimethoxy cinnamate, etc.

the heterocyclic benzodioxol-yl species

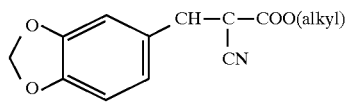

including ethyl α-cyano-4,5-dioxole cinnamate, λ max 361; pentyl α-cyano-4,5-dioxole cinnamate, λ max 361; isoamyl α-cyano-4,5-dioxole cinnamate; t-butyl α-cyano-4,5-dioxole cinnamate; ethyl α-cyano-4,5-dioxole-3-methoxy cinnamate and the like.
and the naphthyl cyano species

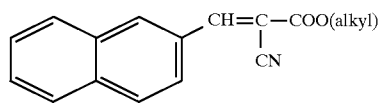

Of the above active sunscreen agents, the dialkoxy α-cyano cinnamate compounds, particularly the isoamyl- and hexyl- α-cyano-3,4-dimethoxy cinnamates, and the quaternized dialkoxy α-cyano cinnamides, particularly the dodecyl tosylate quaternized salt of dimethylamino N-propyl α-cyano 3,4-dimethoxy cinnamide, are preferred. Multiple alkoxy groups on a terminal phenyl radical is found to provide a distinct advantage over the monoalkoxy substituted homolog. It is now discovered that the multiple alkoxy substituents on a terminal phenyl ring provides a significant advantage in resonance of the compound. Specifically the oxygen of an alkoxy in the para (p) position carries a positive charge, whereas the oxygen of an alkoxy in an adjacent or meta (m) position on the ring stabilizes the positively charged p-oxygen by interspacial interaction. In addition to the superior photostability of the present multi-substituted alkoxy cinnamyl compounds, these sunscreening agents possess selective maximum absorptions in the 345–365 nm wavelength range. Hence the present di- or tri-alkoxy substituted cyano cinnamates are significantly more photostable over extended periods of use and offer better protection of the skin and/or hair from the most damaging rays of the sun. Further, as a result of the additional alkoxy substitution in a functional terminal position in their structure, the present sunscreening agents distribute uniformly in traditional cosmetic carriers such as furan, triglycerides, polyethylene glycol, alcohols, e.g. isopropanol, alkanes, e.g. cyclohexane, hexane, octane, etc., vegetable oils and waxes as well as more polar solvents. This advantage enhances their solubility and dispersability for subsequent formulation in aqueous solutions which in turn leads to the formation of a more uniformly dispersed film on the skin which is necessary for good photoprotection.

For use in personal care formulations the present sunscreens can be employed in mixtures with each other or with minor amounts of other known sunscreening agents to extend the absorption range of the later.

In cosmetic or pharmaceutical formulations, the present products can be applied to the skin or hair as a spray, cream, lotion, gel, emulsion or microdispersion and can be used as the sole sunscreening agent or can be employed in admixture with conventional sunscreens to provide effective protection. Generally the concentration of total sunscreening agent in a formulation is between about 0.25 and about 9 wt. %, preferably from about 0.5 to about 6 wt. %, based on the total composition.

The formulation may also include, in addition to a carrier, conventional excipients such as, for example, a thickener, emollient, humectant, diluent, surfactant, hair or skin conditioner, hair dye, preservative, antifoaming agent, fragrance, coloring agent and/or propellant when employed as an aerosol spray. Generally, such excipients can make up to 15 wt. % of the total composition but usually do not exceed 10 wt. %.

The present sunscreening compounds can be economically prepared in a one step process according to the following generic equation

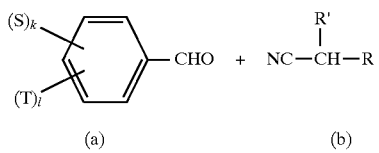

(a)         (b)

where R' is hydrogen or lower alkyl. The mole ratio of aldehyde (a) to cyanide (b) can vary somewhat but is preferably as close to stoichiometry as is convenient to maintain. Within the broad scope of the above equation preparation of the cinnamate sunscreens is described by the general equation:

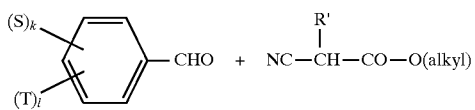

The preparation of the present ketones is shown by

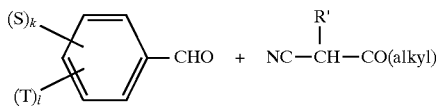

and the preparation of phenyl cinnamonitriles by

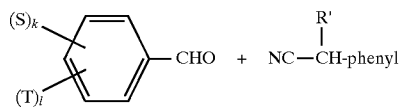

The preparation of the cinnamonitriles can be described by the equation

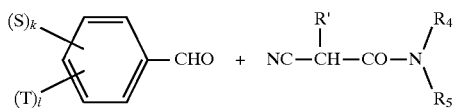

whereas the preparation of the quaternized amides is shown by the equation

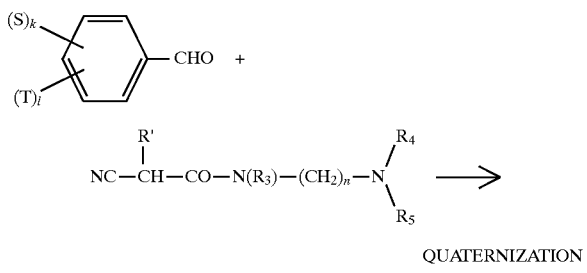

QUATERNIZATION

-continued

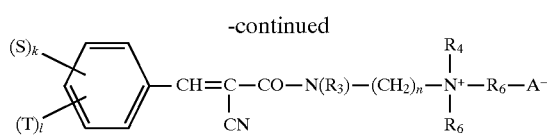

The present compounds are prepared under mild alkaline conditions including a temperature of from about 75° C. to about 150° C., preferably from about 80° C. to about 120° C. over a period of between about 0.5 and about 5 hours, at a pH of from about 9 to about 14, preferably at a pH of 10–12. In this process the aldehyde reactant is introduced in solution and mixed with the cyanide component in about an equimolar proportion. The concentration of aldehyde in solution is conveniently between about 5 and about 70 wt. %, although this concentration can be higher or lower depending on the needs of subsequent formulation in a personal care or topical pharmaceutical composition. Preferred solvents for the aldehyde component include toluene, cyclohexane, octane, ethanol and isopropanol.

The aldehyde and cyanide are reacted in the presence of between about 1 and about 10 wt. % of a deprotonization catalyst such as piperidine, pyridine, sodium methoxide, an organic lithium salt such as lithium diisopropylamide or any other conventional deprotonization catalyst. If desired, the product can be purified by crystallization; however, the products of this invention are generally obtained in good yield and high selectivity.

DESCRIPTION OF THE DRAWINGS

The appended Figures provide meaningful comparisons between the present invention and sunscreens of the prior art.

Figure 1:
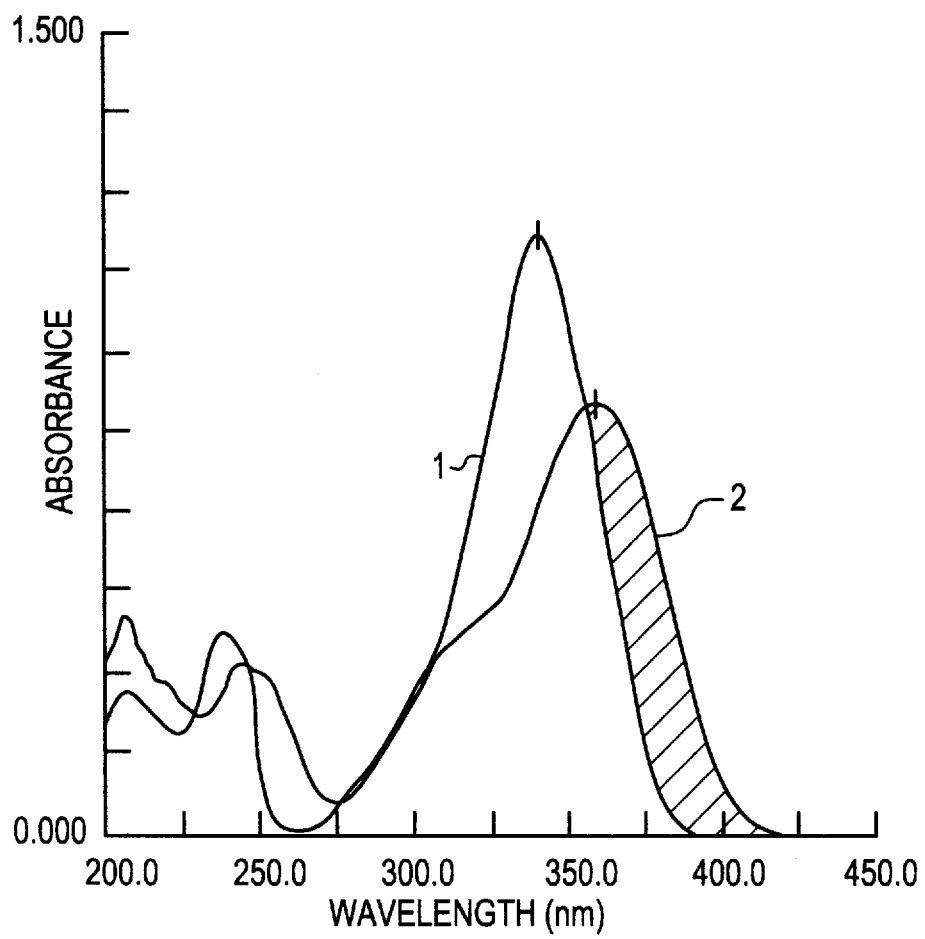
FIG. 1 illustrates the critical difference between the monomethoxy substituted isoamyl cyano cinnamate (curve 1) and the di- methoxy substituted isoamyl cyano cinnamate of the present invention (curve 2). The absorption of the former, having a maximum at about 340 nm falls off down to 260 nm. Surprisingly, the maximum absorption for the present dimethoxy isoamyl cyano cinnamate is maintained at 360 nm and effective light protection is extended up to about 390 nm.
Figure 2:
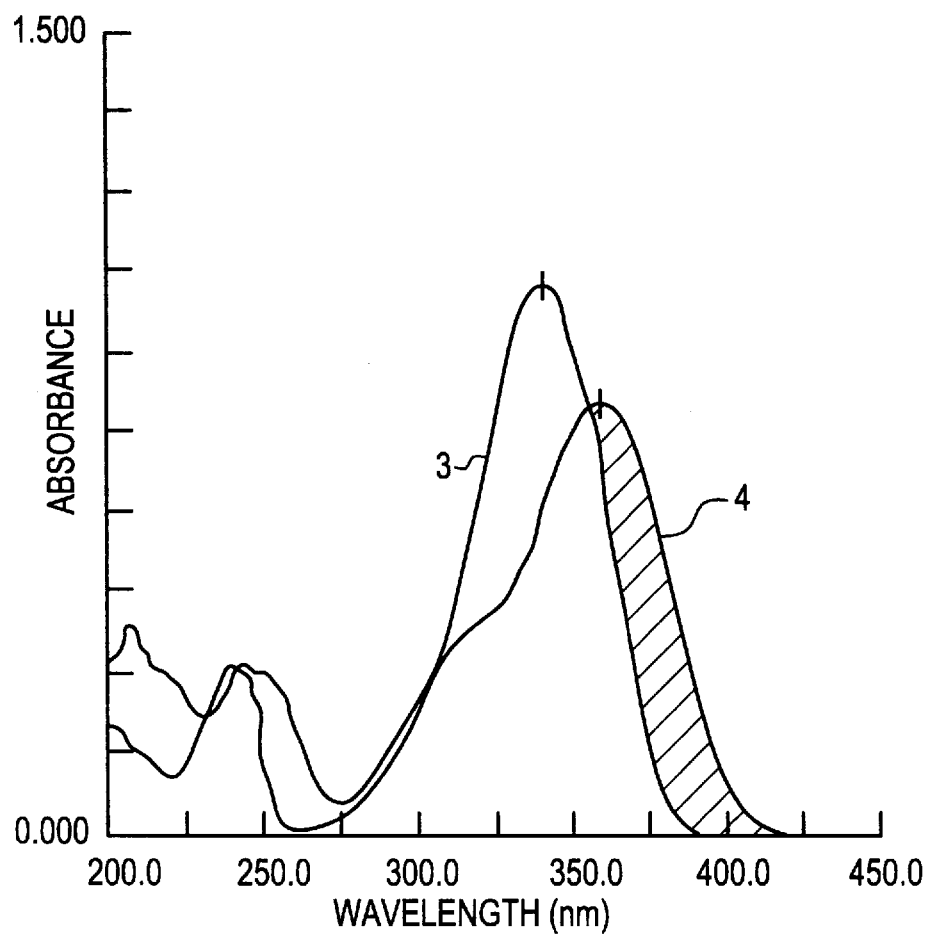
FIG. 2 compares mono methoxy hexyl cyano cinnamate (curve 3) with dimethoxy hexyl cyano cinnamate (curve 4). As can be observed, the monomethoxy substituted ester has a significantly narrower peak absorption range than the correspondingly dimethoxy substituted isoamyl ester so that the dimethoxy ester depicted provides a greater effective absorption in the harmful UV-A II range. The increased absorption is indicated by the hatched area in FIG. 2.
Figure 3:
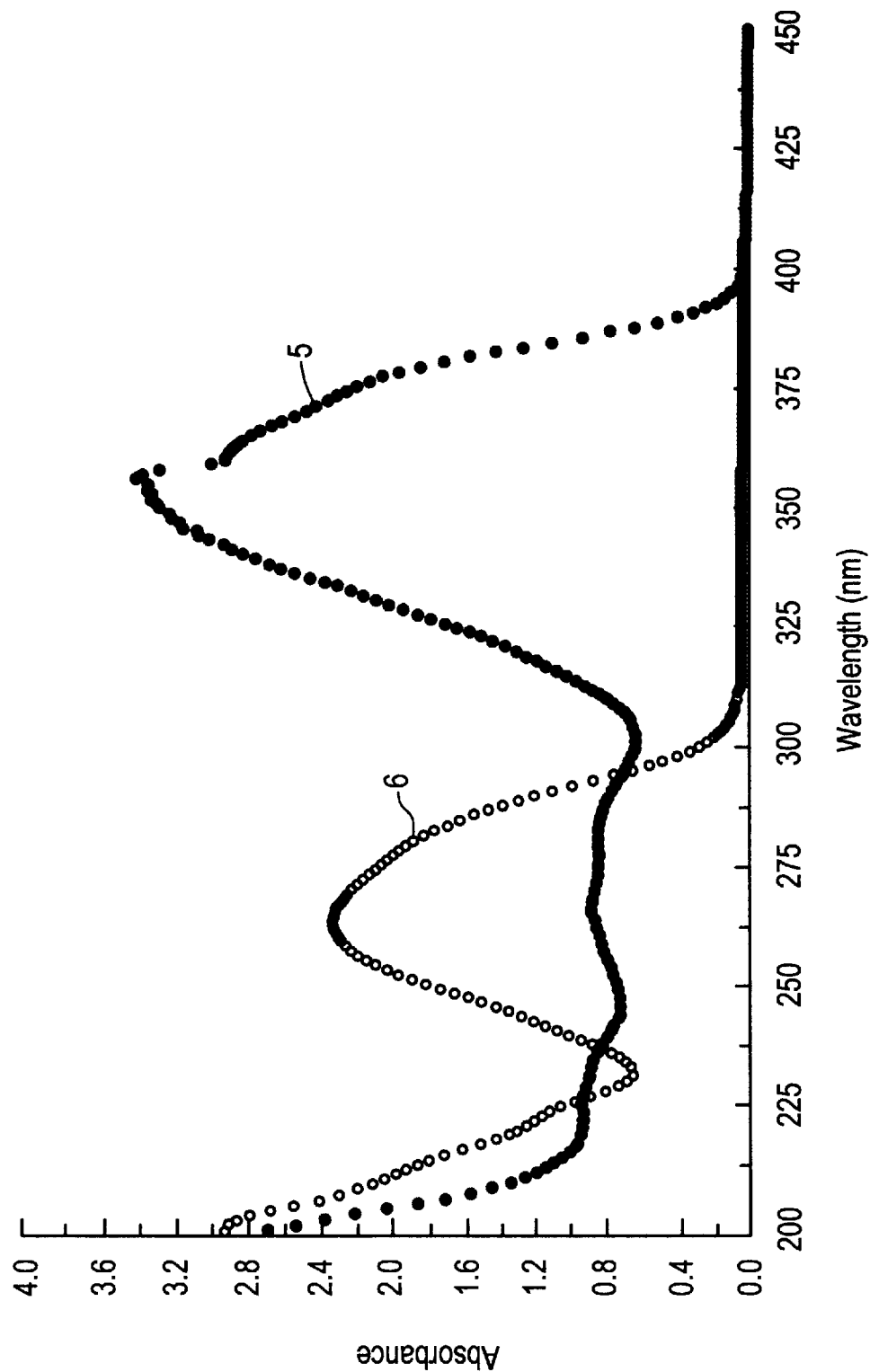
FIG. 3 illustrates the photodegradation of a diketone sunscreen, avobenzone (PARSOL® 1789) in acetonitrile, before illumination (curve 5) and after illumination (curve 6). The rapid absorption decline of PARSOL® 1789 in the wavelength range from about 350 nn after 30 minute illumination detracts from its use as an effective UV-A sunscreen.

Having broadly described the present invention, reference is now had to the accompanying examples which illustrate preferred embodiments and comparisons with the colsest sunscreens of the prior art. It is to be understood that the scope of this invention is not to be limited to the following examples but is defined by the foregoing disclosure and the appended claims.

EXAMPLE 1

Preparation of α-Cyanocinnamates

Into a four neck round bottom glass flask, equipped with a Dean-Stark receiver, a water cooling condenser, a nitrogen purge, an overhead mechanical agitator and a temperature control, was charged 50 g of 3,4-dimethoxy benzaldehyde, 37 g of ethyl cyanoacetate, 2.5 g of piperidine and 150 ml of toluene. The resulting mixture was agitated under reflux for 2 hours at about 110° C. during which time water of the ensuing condensation reaction was intermittently removed. After completion of the reaction, the product ethyl-3,4-dimethoxy-α-cyano cinnamate, was recovered and subjected to washing with 150 ml of deionized water followed by rotary evaporation to remove toluene solvent. The residue was then recrystallized from toluene to produce a pale yellow solid product in 90% yield.

EXAMPLE 2

Example 1 was repeated except that 4-phenyl benzaldehyde was substituted for 3,4-dimethoxy benzaldehyde and 2.6 g of piperidine deprotonization catalyst was employed. The corresponding product, ethyl-α-cyano-4-phenyl cinnamate was recovered as a white solid in 90% yield.

EXAMPLE 3

Example 1 was repeated except that the hexyl ester of cyanoacetic acid was substituted for cyano methyl acetate. The corresponding product, hexyl 3,4-dimethoxy-α-cyano cinnamate was recovered as an off white solid in 93% yield.

EXAMPLE 4

Repetition of Example 1 with 3-methoxy-4-hydroxy benzaldehyde substituted for 3,4-dimethoxy benzaldehyde provides the corresponding ethyl 3-methoxy-4-hydroxy-α-cyano cinnamate as a light yellow solid product in about 85% yield.

EXAMPLE 5

Repetition of Example 1 with the isoamyl ester of cyanoacetic acid substituted for methyl cyano acetate provides the corresponding isoamyl ester of 3,4-dimethoxy-α-cyano cinnamic acid as a pale yellow solid product in greater than 85% yield.

EXAMPLE 6

Preparation of Cyano Cinnamyl Ketones

Repetition of Example 1 with cyanoacetone substituted for methyl cyano acetate provides the corresponding t-butyl ketone of 3,4-dimethoxy-α-cyano cinnamic acid as an off cream colored solid product in greater than 80% yield.

EXAMPLE 7

Preparation of Cyano Cinnamonitriles

Using the equipment of Example 1, 37 g of benzoylacetonitrile and 5 g of sodium methoxide were added to 50 g of 3,4-dimethoxy benzaldehyde dissolved in 100 ml of ethanol. The resulting mixture was agitated for 2 hours at room temperature and for an additional 2 hours at 80° C. The product was cooled and formed a precipitate which was filtered, washed with water and recrystallized from ethanol before drying. The resulting product was recovered as a cream colored solid in 90% yield.

EXAMPLE 8

Preparation of Cyano Cinnamides

Again using the equipment of Example 1, 46 g of dimethylaminopropyl amine was added to 50 g of ethyl cyanoacetate in 50 ml of toluene in the absence of a catalyst. The mixture was agitated under reflux for 2 hours, after which the ethanol by-product was removed. The remaining contents was then cooled to room temperature and 75 g of 3,4-dimethoxy benzaldehyde in 50 ml of toluene and 3.8 g of piperidine catalyst were then added. This mixture was agitated under reflux for 2 hours at about 110° C. during which water of the condensation reaction was removed. Toluene solvent was then removed by rotary evaporation and the dried residue was recrystallized from isopropanol. After washing with about 150 ml of water, the product, dimethylamino N-propyl α-cyano-3,4-dimethoxycinnamide having the structure:

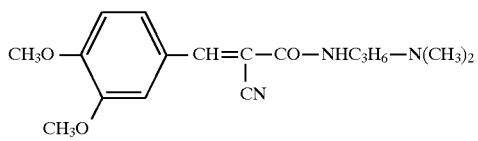

was recovered as a creamy white solid in 92% yield.

EXAMPLE 9

Preparation of Quaternized Cyano Cinnamides

Using the same equipment described above, 56 g of dodecyl tosylate was added to 50 g of the product of Example 8 dissolved in 150 ml of isopropanol. The mixture was agitated and maintained at 100° C. for 2 hours after which the isopropanol was removed by rotary evaporation. The cooled, water washed tosylate quaternized product was recovered as a light yellow solid in quantitative yield.

EXAMPLE 10

Comparative Data on Photostability

The half life of the product of Example 1, namely 3,4-dimethoxy-α-cyano ethylcinnamate, was compared to that of 4-methoxy-α-cyano ethylcinnamate and the results of this comparison are reported in Table I below.

TABLE I

| COMPOUND | HALF LIFE |
| --- | --- |
| ethyl 4-methoxy-α-cyano cinnamate | 1.0 |
| ethyl 3,4-dimethoxy-α-cyano cinnamate | 1.8 |

EXAMPLE 11

The rate of photodegradation of the present dimethoxy α-cyano cinnamates and the results of this comparison are reported in following Table II.

TABLE II

| COMPOUND | HALF LIFE (OVER 10 HOURS) |
| --- | --- |
| isoamyl 4-methoxy-α-cyano cinnamate | 1.07 |
| isoamyl 3,4-dimethoxy-α-cyano cinnamate | 1.45 |
| hexyl 4-methoxy-α-cyano cinnamate | 1.0 |
| hexyl 3,4-dimethoxy-α-cyano cinnamate | 1.44 |

The astonishing results of the comparisons reported in Examples 10 and 11 where half-life of the present compounds was almost doubled emphasizes the discovery of this invention concerning the need for a proton stabilizer acting on a mono alkoxy substituted phenyl ring in the cyano cinnamate sunscreens.

What is claimed is:

1. A photostable sunscreening agent soluble in polar organic solvents having the formula:

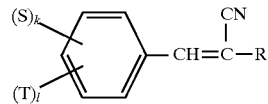

wherein

R is —CO(R$_2$) or phenyl optionally substituted with lower alkyl and/or lower alkoxy;

R$_2$ is C$_1$ to C$_{18}$ —alkyl, —(C$_1$ to C$_{18}$ alkyl),

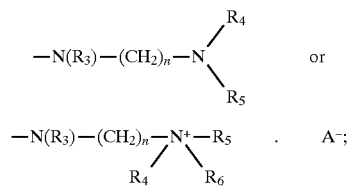

n has a value of from 2 to 8;

S and T each independently are hydroxy, lower alkyl, lower alkoxy or, when R$_2$ is alkyl or alkoxy, S may also be phenyl and when R$_2$ is alkoxy, T is alkoxy or S+T taken with the phenyl ring form a naphthyl radical or a fused benzodioxol-5-yl heterocyclic radical;

k+l has a value of from 0 to 3 with the proviso that, when R$_2$ is —O(alkyl), T is —O(lower alkyl) and the value of l is at least 2;

R$_3$ is hydrogen or lower alkylene;

R$_4$, R$_5$ and R$_6$ are each independently C$_1$ to C$_{18}$ alkyl, C$_1$ to C$_4$ alkoxy or any one of R$_4$, R$_5$ and R$_6$ independently may be phenyl and A is an anion.

2. The sunscreening agent of claim 1 wherein R is —CO(alkyl).

3. The sunscreening agent of claim 1 wherein R is COO(alkyl).

4. The sunscreening agent of claim 3 wherein S and T are each alkoxy and k and l each have a value of 1.

5. The sunscreening agent of claim 4 wherein said alkoxy of S and T is methoxy.

6. The sunscreen of claim 3 wherein said alkyl is a radical containing at least 4 carbon atoms and has a branched structure.

7. The sunscreening agent of claim 5 which is isoamyl 3,4-dimethoxy-α-cyano cinnamate.

8. The sunscreening agent of claim 1 wherein R is a phenyl ring.

9. The sunscreening agent of claim 8 wherein said phenyl ring contains 2 alkoxy substituents.

10. The sunscreening agent of claim 1 wherein S and T taken with the phenyl ring forms a heterocyclic benzodioxolyl fused ring.

11. The sunscreening agent of claim 1 wherein S and T taken with the phenyl ring forms a naphthyl ring.

12. The sunscreening agent of claim 1 wherein R$_2$ is

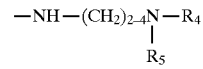

or a quaternized salt thereof.

13. The sunscreening agent of claim 12 wherein R$_4$ and R$_5$ are each lower alkyl.

14. The sunscreening agent of claim 13 wherein said agent is quaternized compound.

15. The sunscreening agent of claim 14 wherein said quaternizing agent is a C$_{4-14}$ alkyl tosylate.

16. A sunscreening formulation containing a sunblocking amount effective to absorb lumination in a range above 340 nm wavelength of any one of the agents of claims 1, 2, 3 and 12 above or mixtures thereof.

17. A sunscreening formulation containing a conventional sunscreening agent and a sunscreening agent of claim 1 in an amount effective to absorb lumination in the range above 340 nm wavelength.

18. The process of applying to a photo unstable substrate the sunscreening formulation of claim 16.

19. The process of applying to a photo unstable substrate the sunscreening formulation of claim 17.

20. The process of synthesizing the sunscreening agent of claim 1 which comprises (i) mixing the components

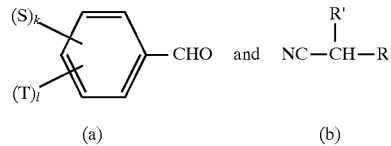

where

R' is hydrogen or lower alkyl, in a mutual solvent and in the presence of a deprotonation catalyst at a temperature of from about 75° to about 150° C. for a period of from about 0.5 to about 5 hours at a pH of 9–14 to form a solid product having a maximum absorption above 340 nm;

(ii) cooling the product, removing the solvent and (iii) recovering the product of the process.

21. The process of claim 20 wherein at least one of S and T is lower alkoxy.

22. The process of claim 21 wherein S and T are each CH$_2$O— and k and l each have a value of 1.

23. The process of claim 20 wherein the product of step (ii) is recrystalized before recovery.

* * * * *